US007354596B1

(12) United States Patent
Banovetz et al.

(10) Patent No.: US 7,354,596 B1
(45) Date of Patent: *Apr. 8, 2008

(54) ANTI-MICROBIAL AGENT DELIVERY SYSTEM

(75) Inventors: John P. Banovetz, Minneapolis, MN (US); Jeffry L. Jacobs, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/070,975

(22) Filed: May 1, 1998

(51) Int. Cl.
*A01N 25/28* (2006.01)

(52) U.S. Cl. ............... 424/408; 424/405; 424/406; 424/407; 424/409; 424/417; 424/419; 424/421; 424/617; 424/635

(58) Field of Classification Search ............. 424/400, 424/401, 402, 405, 407, 408, 411, 412, 413, 424/414, 417, 419, 421, 489, 490, 494, 497, 424/500, 501, 473
See application file for complete search history.

(56) References Cited

U.S. PATENT DOCUMENTS

| | | | |
|---|---|---|---|
| 3,528,842 A | 9/1970 | Skadulis ............... 117/27 |
| 3,598,627 A | 8/1971 | Klimboff .............. 117/25 |
| 3,691,140 A | 9/1972 | Silver |
| 3,884,706 A | 5/1975 | Little ............... 106/15 R |
| 3,888,176 A | 6/1975 | Horai, Jr. et al. ....... 106/15 AF |
| 3,888,682 A | 6/1975 | Nelson ............... 106/15 AF |
| 3,888,683 A | 6/1975 | Horai, Jr. et al. ....... 106/15 AF |
| 3,888,684 A | 6/1975 | Little ............... 106/15 AF |
| 3,894,877 A | 7/1975 | Nelson ............... 106/18 |
| 3,928,546 A | 12/1975 | Guzzo |
| 3,975,280 A * | 8/1976 | Hachmann et al. ....... 252/102 |
| 3,985,540 A * | 10/1976 | Fein et al. ............ 504/152 |
| 4,092,441 A | 5/1978 | Meyer et al. ............ 427/37 |
| 4,166,152 A | 8/1979 | Baker et al. |
| 4,244,836 A | 1/1981 | Frensch et al. |
| 4,290,426 A * | 9/1981 | Luschen et al. |
| 4,310,509 A | 1/1982 | Berglund et al. ......... 424/28 |
| 4,353,962 A | 10/1982 | Himel et al. |
| 4,360,611 A | 11/1982 | Wakimoto et al. ........ 523/216 |
| 4,415,615 A | 11/1983 | Esmay et al. |
| 4,495,318 A | 1/1985 | Howard |
| 4,602,959 A | 7/1986 | Kurita et al. ............ 106/18.32 |
| RE32,356 E | 2/1987 | Cardarelli ............. 424/78 |
| 4,690,825 A | 9/1987 | Won |
| 4,707,355 A | 11/1987 | Wilson |
| 4,786,696 A | 11/1988 | Bohnel |
| 4,833,179 A | 5/1989 | Young et al. ............ 522/183 |
| 4,952,650 A | 8/1990 | Young et al. ............ 526/194 |
| 4,968,562 A | 11/1990 | Delgado |
| 4,983,389 A * | 1/1991 | Levy .................. 424/404 |
| 4,988,467 A | 1/1991 | Holdsworth et al. |
| 4,994,322 A | 2/1991 | Delgado et al. |
| 5,045,569 A | 9/1991 | Delgado |
| 5,053,436 A | 10/1991 | Delgado |
| 5,118,750 A | 6/1992 | Silver et al. |
| 5,215,818 A | 6/1993 | Silver et al. |
| 5,261,169 A * | 11/1993 | Williford ............. 36/43 |
| 5,264,484 A | 11/1993 | Arai et al. ............ 524/714 |
| 5,286,493 A | 2/1994 | Oshlack et al. |
| 5,316,824 A | 5/1994 | George et al. .......... 428/145 |
| 5,356,664 A | 10/1994 | Narayan et al. ......... 427/186 |
| 5,366,767 A | 11/1994 | Howard ............... 427/294 |
| 5,382,475 A | 1/1995 | Kayser ............... 428/403 |
| 5,391,417 A | 2/1995 | Pike .................. 428/143 |
| 5,411,803 A | 5/1995 | George et al. .......... 428/403 |
| 5,415,919 A | 5/1995 | George et al. .......... 428/145 |
| 5,427,793 A | 6/1995 | Bigham et al. .......... 424/404 |
| 5,460,817 A | 10/1995 | Langley et al. |
| 5,492,696 A * | 2/1996 | Price et al. ............ 424/417 |
| 5,502,108 A | 3/1996 | Silver et al. |
| 5,503,839 A | 4/1996 | Saguchi et al. |
| 5,508,313 A | 4/1996 | Delgado et al. |
| 5,571,617 A | 11/1996 | Cooprider et al. |
| 5,603,961 A | 2/1997 | Suzuki et al. |
| 5,616,315 A * | 4/1997 | Masterman et al. ....... 424/54 |
| 5,639,476 A | 6/1997 | Oshlack et al. |
| 5,639,843 A | 6/1997 | Babirad et al. .......... 528/9 |
| 5,667,806 A * | 9/1997 | Kantor ............... 424/484 |
| 5,849,325 A * | 12/1998 | Heinecke et al. ........ 424/443 |
| 5,908,693 A * | 6/1999 | Delgado et al. ......... 428/343 |

(Continued)

FOREIGN PATENT DOCUMENTS

EP 0 023 828 2/1981

(Continued)

OTHER PUBLICATIONS

American Heritage Dictionary, "Amorphous", p. 103, 1982.*

(Continued)

*Primary Examiner*—Neil S. Levy
(74) *Attorney, Agent, or Firm*—Colene H. Blank

(57) ABSTRACT

A delivery system for delivering an anti-microbial agent to a surface in a time release manner. The delivery system includes one or more polymeric particles (e.g., microspheres, core/shell particles, latexes, porogens, cryogenically ground beads, condensation polymer particles, flakes, etc.) and at least anti-microbial agent attached thereto. The anti-microbial agents may or may not be soluble in the polymeric particle or in the monomeric precursor used to make the polymeric particle. The anti-microbial agent can be incorporated into the microsphere using either a post polymerization addition process or an in situ addition process. The delivery system can be fashioned to provide characteristics that are application specific. Examples of such delivery systems include but are not limited to substrates (such as tapes, sheets of material and the like) coated with the releasably loaded polymeric particles, sprayable dispersions or suspensions of these polymeric particles and the like.

19 Claims, No Drawings

U.S. PATENT DOCUMENTS 6,214,331 B1 * 4/2001 Vanderhoff et al. ...... 424/78.17
6,471,975 B1 * 10/2002 Banovetz et al. ........... 424/408

FOREIGN PATENT DOCUMENTS

| EP | 0 201 214 | 11/1986 |
|----|-----------|---------|
| EP | 0 203 724 | 12/1986 |
| EP | 0 227 987 | 7/1987 |
| EP | 0 371 635 | 6/1990 |
| EP | 0 594 440 B1 | 4/1994 |
| EP | 0 679 333 | 11/1995 |
| FR | 2 155 166 | 5/1973 |
| JP | 58-12255 | 3/1983 |
| JP | 81-65210 | 6/1996 |
| WO | 81/02505 | 9/1981 |
| WO | 92/10285 | 6/1992 |
| WO | 95/13698 | 5/1995 |
| WO | 96/01048 | 1/1996 |
| WO | 96/01280 | 1/1996 |
| WO | 97/46633 | 12/1997 |
| WO | 97/46634 | 12/1997 |
| WO | 98/17481 | 4/1998 |
| WO | 98/44912 | 10/1998 |

OTHER PUBLICATIONS

"Industrial Antimicrobial Agents," Encyclopedia of Chemical Technology, Fourth Ed., vol. 14, John Wiley & Sons, pp. 174-199, (1995).

Yüksel et al., "Interaction between nicardipine hydrochloride and polymeric microspheres for a controlled release system," International Journal of Pharmaceutics, 140, pp. 145-154, (1996).

"Biological Activity," Encyclopedia of Polymer Science and Engineering, vol. 2, John Wiley & Sons, pp. 259, 261-262, (1985).

"Organometallic Polymers," Encyclopedia of Polymer Science and Engineering, vol. 10, John Wiley & Sons, pp. 545, 589, (1985).

"Coatings," Encyclopedia of Polymer Science and Engineering, vol. 3, John Wiley & Sons, pp. 656-657, (1985).

* cited by examiner

ANTI-MICROBIAL AGENT DELIVERY SYSTEM

FIELD OF THE INVENTION

This invention relates to systems for delivering active anti-microbial agents, particularly, to a polymer particle containing an active anti-microbial agent which allows the anti-microbial agent to be released over time, more particularly, to an elastomeric polymer particle (e.g., a microsphere) having an active anti-microbial agent incorporated therein so as to be time released in the presence of water and, even more particularly, to such an anti-microbial delivery system for use on surfaces where microbes can grow, such as on various portions of buildings and on other related structures.

BACKGROUND OF THE INVENTION

Microbes (e.g., algae, bacteria, fungus, mildew and mold) typically grow on warm wet surfaces. The presence and growth of such microbes is usually undesirable. For example, in the roofing industry, the discoloration of roofing materials (e.g., asphalt, wood or plastic shingles; ceramic or metal tile; slate; bituminous roofing membranes; metal sheeting; roll roofing; etc) is largely attributable to the growth of various types of blue-green algae, most commonly *Gloeocapsa*, and *Scytonema*, as well as various types of green algae in certain environments. Current approaches to solve this problem include such things as regular roof cleanings and installation of zinc metal strips on the roof. Another approach, particularly applicable to conventional asphalt shingles, is the incorporation of copper releasing granules along with standard color granules applied to the surface of the asphalt mat during the shingle manufacturing process. There are several disadvantages associated with each of these approaches. Roof cleanings, especially in southern regions of the US, can, be necessary on at least an annual basis to maintain a clean roof, since this approach provides no means of preventing the return of the microorganisms. Furthermore, the cleaning process may actually damage or shorten the life of the roof. Zinc strips may provide an algae free roof, but are often aesthetically objectionable, since they are clearly visible on the roof. Shingles with the copper containing granules can be effective for long terms without detracting from the desired visual effect, but this approach fails to address the need to protect existing roofs which were not originally covered with such shingles. Additionally, while well suited for use by the manufacturer of asphalt shingles, copper containing granules are much less applicable for other types of roofing materials (e.g., wood shingles, ceramic tile, slate, etc.). In addition, the prior art has failed to address the need for an anti-microbial delivery system which is practical and compatible with other building related structures (e.g., air conditioning and heating ducts, walls, ceilings, exterior siding, decks, patios, etc.) or other structures (e.g., fences, the inside of refrigeration units, cooling towers, animal cages, ductwork etc.).

Thus, there exists a need for an effective and versatile delivery system for an anti-microbial agent which can be used on existing roofs, as well as in the manufacture of new roofing materials, and on other structures.

SUMMARY OF THE INVENTION

The present invention provides an anti-microbial delivery system for delivering an anti-microbial agent to a surface in a time release manner. The delivery system includes one or more polymeric particles (e.g., microspheres, core/shell particles, latexes, porogens, cryogenically ground beads, condensation polymer particles, flakes, etc.) and at least one anti-microbial agent attached thereto. The anti-microbial agents may or may not be soluble in the polymeric particle or in the monomeric precursor used to make the polymeric particle. The anti-microbial agent can be incorporated into the microsphere using either a post polymerization addition process or an in situ addition process. Loading polymeric particles with a releasable anti-microbial agent provides a delivery device that can be fashioned to provide characteristics that are application specific. Examples of such delivery devices include but are not limited to substrates (such as tapes, sheets of material and the like) coated with the releasably loaded polymeric particles, sprayable dispersions or suspensions of these polymeric particles and the like.

In one aspect of the present invention such a delivery system is provided which comprises a polymeric particle containing an anti-microbial agent. The anti-microbial agent is incorporated within the polymeric particle so as to be releasable from the boundary defined by the polymeric particle in an effective amount over time, when the polymeric particle is in the presence of water.

In another aspect of the present invention, a method of applying an anti-microbial agent is provided. The method comprises the steps of providing a polymeric particle having an anti-microbial agent attached thereto so as to be releasable from the polymeric particle in an effective amount over time, when the polymeric particle is in the presence of water; and applying the polymeric particle to a surface of a structure.

In yet another aspect of the present invention, a method of forming an anti-microbial delivery system is provided which comprises the steps of: (a) providing a polymerized elastomeric microsphere precursor; (b) blending the polymerized elastomeric microsphere precursor with a releasable anti-microbial agent or mixture of agents, wherein the releasable anti-microbial agent or mixture of agents is optionally dissolved in a solvent and such that the releasable anti-microbial agent is absorbed within the boundaries of the polymerized elastomeric microsphere precursors and; (c) optionally, removing the solvent.

In an additional aspect of the present invention, another method of forming an anti-microbial delivery system is provided which comprises the steps of: (a) forming an oil phase comprising at least one oil soluble monomer, an oil soluble initiator and a releasable anti-microbial agent or a portion of the releasable anti-microbial agent in a water phase comprising at least one suspension stabilizer or surfactant; (b) initiating polymerization of the oil phase in the water phase; and (c) optionally, adding remaining oil soluble releasable anti-microbial agent.

Polymeric particles (e.g., microspheres, core/shell particles, latexes, porogens, cryogenically ground beads, condensation polymer particles, flakes, etc.) according to the present invention can be made tacky or tack-free, with a solid or hollow morphology. The polymer particles can incorporate pendant hydrophilic polymeric or oligomeric moieties, to make at least an outer region of the polymer particle more hydrophilic (i.e., more water absorbent), thereby possibly affecting the release rate of the anti-microbial agent. Polymeric particles in the form of microspheres can have a diameter in the range of from about 0.5 microns to about 300 microns.

Elastomeric microspheres can be made using colloidal polymerization techniques, such as suspension polymerization. Colloidal polymerization techniques rely on the use of stabilizing agents, such as surfactants, to avoid flocculation or agglomeration of the suspended polymer microspheres. The surfactant is used to stabilize the size of the suspended globules or droplets of monomer before polymerization and, thus, the size of the resulting polymer microspheres. The surfactant also keeps the monomer droplets and polymer microspheres separate during the polymerization.

Surprisingly, the addition of anti-microbial agents, particularly inorganic particles, during the preparation of the exemplary elastomeric acrylate microspheres was found to result in a stable dispersion of the microspheres, even with high levels of the anti-microbial agent being added to the suspension solution and, thereby, incorporated into the microsphere (e.g., up to about 40% by weight of the microsphere, for $Cu_2O$ particles). It is believed that the addition of such anti-microbial agents during the preparation of elastomeric vinyl ester microspheres will also, surprisingly, result in a stable dispersion of the microspheres, even with high levels of the agent.

Before the present invention, it was believed that the use of anti-microbial agents, particularly inorganic particles, in the formation of either acrylate or vinyl ester based microspheres would not result in a stable dispersion of the microspheres. This belief was based, at least in part, on the observation that the presence of latex particles in solution, during the suspension polymerization of the microspheres, diverted surfactant away from the monomer during polymerization (i.e., the latex depletion effect). In other words, it was believed that such anti-microbial agents would cause coagulation of the polymer, generated from the polymerization of the monomer droplets, rather than forming discreet polymer microspheres. Coagulation can actually occur if the proper surfactant is not chosen. Therefore, it is also desirable for the surfactant to be chosen so as not to compete with the monomer for the surface of the inorganic (e.g., $Cu_2O$) particles. Alternatively, one may use additional surfactant to compensate for the additional surface area of the inorganic particles or use a surface treatment on the (e.g., $Cu_2O$) particles such as a silane, a titanate, or even an organic acid, such as oleic acid, which has a higher affinity for the particle surface than the polymerization surfactant.

Inorganic particles have been used as dispersing or stabilizing agents in suspension polymerization processes to form polymer particles (i.e., thermoplastic elastomeric microspheres), as evidenced by U.S. Pat. Nos. 4,952,650; 4,833,179; and 4,360,611, the disclosures of which are herein incorporated by reference. However, these inorganic particle stabilizing agents did not become incorporated into the resulting polymer particles and were either not known and/or expected to exhibit any anti-microbial properties. The role of the inorganic particles in the present invention, in contrast, is not as a stabilizer or dispersing agent for the suspended polymer particles. The inorganic particles used in the present invention are actually incorporated into the polymeric particle (e.g., elastomeric microsphere) and are used for their anti-microbial properties, not to avoid agglomeration of the monomer droplets or polymer particles.

As used herein:

"anti-microbial" means a biologically active material that affects the life processes (e.g., inhibits or prevents the implantation, growth and/or life) of a living micro-organism (e.g., algae, fungus, mildew, mold, bacteria);

"effective amount" means an amount effective to allow the present anti-microbial delivery system to achieve a desired affect on the living micro-organism. The amount that constitutes an effective amount varies according to the particular anti-microbial agent being employed, the desired affect on the micro-organism, the desired duration of treatment, the release rate, the surface area and location where the anti-microbial delivery system is to be placed, and the selection of the components of the anti-microbial delivery system. Accordingly, it is not practical to enumerate particularly preferred amounts but such can be readily determined by those skilled in the art with due consideration of these and other appropriate factors;

"elastomeric" means amorphous or noncrystalline materials that can be stretched to at least twice their original length and that will retract rapidly to substantially their original dimensions upon release of the force;

"partially water miscible" means the solubility of the compound is less than about 98% but greater than about 0.5% by weight (e.g., if 1 gram of the compound is put in 100 grams of water, in the range of from about 0.005 grams to about 0.98 grams would dissolve);

"releasable" means that when the anti-microbial delivery device is placed in its intended environment of use (e.g., on a roof), at least some effective amount of the anti-microbial agent moves out of the microsphere over time;

"solvent" means conventional organic solvents generally used in the industry which include, for example, toluene, heptane, ethyl acetate, methyl ethyl ketone, acetone, and mixtures thereof;

"water immiscible" means the solubility of the compound is less than 0.5% by weight; and "the insolubility of $Cu_2O$ in water" means that the solubility is at least less than approximately 1000 ppm (at 25 C).

The objectives, features, and advantages of the present invention will become apparent upon consideration of the present specification.

DETAILED DESCRIPTION OF PREFERRED EMBODIMENTS

Although the present invention is herein described in terms of specific embodiments, it will be readily apparent to those skilled in this art that various modifications, re-arrangements, and substitutions can be made without departing from the spirit of the invention. The scope of the present invention is thus only limited by the claims appended hereto.

It has been discovered that polymeric particles (e.g., microspheres, core/shell particles, latexes, porogens, cryogenically ground beads, condensation polymer particles, flakes, etc.), particularly elastomeric microspheres, can be employed in a system for delivering anti-microbial materials or agents that are useful in a wide variety of applications. The polymer particle contains an inorganic, organic or combination of anti-microbial agents which are slowly released from the polymer particle over time to prevent long term growth of microorganisms. One particular application described in detail herein is the use of elastomeric microspheres to deliver materials with anti-microbial properties for exterior roofing applications.

When the active agent(s) are incorporated within a polymeric particle, a delivery system capable of a controlled release of the active agent is produced. The preferred method of incorporating the anti-microbial agent(s) is by dispersing the agent in a monomer or mixture of monomers prior to polymerization of the monomer(s) into polymer particles thereby trapping the agent in the polymer particles during polymerization. It may also be desirable to add the agent to the polymer particles after polymerization by a post-add process, for example, by allowing the agent to be absorbed into part or all of the polymer particle or by swelling the particle with a fugitive swelling agent, allowing migration of the active agent into the particle to occur, and removing the swelling agent.

The polymer particles can be made tacky (i.e., with pressure sensitive adhesive properties) or non-tacky. Its degree of crosslinking can determine the tackiness of the polymer particle. The crosslinking level can also affect the swellability of the polymer particle. To ensure a high degree of polymer particle swelling, it is desirable to use appropriate levels of crosslinker. Crosslinking may also be important in achieving the desired release rate of the incorporated anti-microbial agent. The tacky or non-tacky polymer particle can be solid or hollow (i.e., contain one or more voids) and is generally crosslinked at least to an extent such that it tends to stay in particle form throughout the processing and use.

Microspheres

Inherently tacky pressure sensitive adhesive elastomeric microspheres have been useful in repositionable pressure sensitive adhesive applications and there are numerous references discussing the preparation and/or use of such microspheres. The term repositionable refers to the ability of the tacky microsphere to be repeatedly adhered to and removed from a substrate without substantial loss of adhesion capability. Typically, pressure sensitive adhesive microspheres are prepared via suspension polymerization of one or more free radically polymerizable monomers in the presence of surfactants and/or suspension stabilizers. For the suspension polymerization process, it is desirable for the anti-microbial agent to be relatively insoluble in water. At the same time, the agent must have some degree of solubility in water in order to be releasable. So, a desired release rate is dependent, at least in part, on (1) the coefficient of diffusion of the agent through the polymeric microsphere material and (2) the solubility of the anti-microbial agent in water. It is also desirable for the anti-microbial agents to be at least sufficiently stable and unreactive so as not to prevent polymerization, to not significantly interfere with the surfactant, and to be dispersible in the monomer phase, all at levels capable of releasing an effective amount. Furthermore, desirable polymer compositions and anti-microbial agents are also substantially non reactive so as not to substantially degrade or prevent release of the anti-microbial agent. For example, acid groups are typically not compatible with $Cu_2O$ while basic groups typically are.

Choice of surfactants and/or suspension stabilizers and their specific combinations with specific monomers can determine suspension stability, desired particle morphology, performance characteristics, and the like. The surfactant should be chosen so as not to compete with the monomer for the surface of the inorganic (e.g., $Cu_2O$) particles. It is desirable for the surfactant to be substantially non-reactive with or otherwise not degrade the chosen anti-microbial agent (e.g., by not breaking down a metal oxide agent into its ions).

Various copolymerizable monomers, suspension stabilizers and/or surfactants may be combined to modify the properties of these suspension polymerized microspheres. For example, microspheres containing one or more internal voids or cavities, as described in the art, display different performance characteristics.

Copolymerizable or otherwise incorporated oligomeric and polymeric additives can also be employed in suspension polymerized microspheres to alter performance characteristics. Hydrophilic oligomers and polymers can be included in suspension polymerizable adhesive microsphere formulations to provide improved microsphere stability during synthesis and loading and, in some formulations, water dispersibility.

Preparation of Microspheres

It is believed that polymeric microspheres of the present invention can be prepared by suspension, dispersion, direct emulsion and modified emulsion techniques. Preferably, the present polymeric microspheres are prepared according to the suspension polymerization methods described in, for example, U.S. Pat. Nos. 3,691,140; 4,166,152; 4,495,318; 4,786,696; 4,988,467; 5,045,569; 5,508,313; and 5,571,617, the disclosures of which are all incorporated herein by reference. The preferred polymeric microspheres are acrylate or vinyl ester microspheres. It is also preferred that the present microspheres be swellable and elastomeric.

In preferred suspension polymerization methods, the acrylate or vinyl ester microspheres can typically be prepared by forming an oil phase comprising (meth)acrylic acid ester and/or vinyl ester monomers and an oil soluble free radical initiator in a water phase that comprises an aqueous medium having at least one suspension stabilizer or surfactant. General examples of polymer compositions for the microspheres include 70–100% low Tg monomer, 30–0% polar comonomer, 0–3% crosslinker, and 0–10% ionic comonomer; 90–100% low Tg monomer, 10–0% polar comonomer, and 0–3% crosslinker; and 97–100% low Tg monomer and 0–3% crosslinker. Examples of surfactants may include anionic surfactants such ammonium lauryl sulfate or sodium dodecylbenzosulfonate (effective with organic anti-microbial agents or acid stable inorganics), non-ionic surfactants such as ethylene oxide/propylene block copolymers, and non-ionic polymeric surfactants such as poly(vinyl alcohol).

The oil phase can, optionally, also contain free radically polymerizable polar co-monomers. Depending on the types and amounts of monomer and co-monomers, crosslinking agents, stabilizers, surfactants, reaction conditions, and other composition and process alternatives employed, these microspheres can be hollow (i.e., having at least one internal void or cavity) or solid (i.e., having no internal voids or cavities); tacky or tack free; water or solvent dispersible; lightly or highly crosslinked; and can have a range of diameters (from about 0.5 to about 300 microns) and a range of polymeric morphologies.

(Meth)acrylic acid ester monomers used in elastomeric acrylate microspheres are, preferably, monofunctional unsaturated (meth)acrylate esters of non-tertiary alkyl alcohols. The alkyl groups of these alcohols, preferably, contain from 4 to 14 (more preferably from 4 to 10) carbon atoms. Examples of useful monomers include sec-butyl acrylate, n-butyl acrylate, isoamyl acrylate, 2-methylbutyl acrylate, 4-methyl-2-pentyl acrylate, 2-ethylhexylacrylate, isooctyl acrylate, isononyl acrylate, isodecyl methacrylate, isodecyl acrylate, dodecyl acrylate, teradecyl acrylate and mixtures thereof. Particularly preferred are n-butyl acrylate, sec-butyl acrylate, isoamyl acrylate, 2-ethylhexyl acrylate, isooctyl acrylate, isononyl acrylate, isodecyl acrylate, and mixtures thereof. Of these, isooctyl acrylate and 2-ethylhexyl acrylate are the most preferred.

Vinyl ester monomers useful for providing the elastomeric vinyl ester microspheres are unsaturated vinyl esters derived from linear or branched carboxylic acids having 1–14, and preferably 7 to 12, carbon atoms (not counting the carboxyl carbon atom). Suitable vinyl ester monomers include vinyl propionate, vinyl pelargonate, vinyl hexanoate, vinyl caprate, vinyl 2-ethylhexanoate, vinyl octanoate, vinyl decanoate, vinyl laurate, and mixtures thereof. Particularly preferred are vinyl caprate, vinyl 2-ethylhexonate, vinyl laurate, and mixtures thereof.

(Meth)acrylate ester or other vinyl monomers which, as homopolymers, have glass transition temperatures higher than about −20° C. (e.g., ethyl acrylate, tert-butyl acrylate, isobornyl acrylate, butyl methacrylate, vinyl acetate, acrylonitrile, mixtures thereof and the like) may be used in conjunction with one or more of the (meth)acrylate and vinyl ester monomers which, as homopolymers, have glass transition temperatures lower than −20° C., provided that the glass transition temperature of the resulting microspheres is below about 0° C.

Elastomeric acrylate or vinyl microspheres useful in the present inventions can further comprise a free radically polymerizable polar comonomer that is copolymerizable with the (meth)acrylic acid ester or vinyl ester monomer. The free radically polymerizable polar comonomers may be added to improve or modify the cohesive strength, storage stability adhesion to polar surfaces, and glass transition temperature of the microspheres. It is preferred that the polar monomer be incorporated in an amount of no more than about 1 to 20 parts by weight. If too much of the polar monomer is used, water phase polymerization (i.e., the formation of latex particles) can occur.

In addition to their copolymerizability with the (meth) acrylic acid ester or vinyl ester monomer, the free radically polymerizable polar comonomers are monomers that are both oil and water soluble and include one of the following polar substituents: amide, nitrile, hydroxyl, and carboxylic acid (including acid salt) groups. Suitable polar monomers include monoolefinic monocarboxylic acids, monoolefinic dicarboxylic acids, salts of the two preceding acids, acrylamides, N-substituted acrylamides, N-vinyl lactams, and mixtures thereof. Representative examples of these classes of useful polar monomers include acrylic acid, methacrylic acid, itaconic acid, crotonic acid, maleic acid, fumaric acid, sulfoethyl methacrylate, N-vinyl pyrrolidone, N-vinyl caprolactam, acrylamide, t-butyl acrylamide, dimethylamino ethyl acrylamide, N-octyl acrylamide, hydroxy ethyl acrylate, and hydroxy ethyl methacrylate. Also useful are ionic monomers such as sodium methacrylate, ammonium acrylate, sodium acrylate, trimethylamine p-vinyl benzimide, N,N-dimethyl-N-(beta-methoxy-ethyl)ammonium propionate betaine, trimethylamine methacrylamide, 1,1-dimethyl-1-(2,3-dihydrooxylpropyl)amine methacrylamide, and mixtures thereof. Particularly preferred are acrylic acid, sodium acrylate, N-vinyl pyrrolidone, and mixtures thereof.

The elastomeric microspheres useful in the present invention may also contain a multifunctional free-radically polymerizable crosslinking agent. Such crosslinking agents can enhance the cohesive strength and solvent insolubility of the individual microspheres by internally crosslinking the microsphere. "Multifunctional" refers to crosslinking agents that possess two or more free-radically polymerizable olefinically unsaturated groups. Useful multifunctional crosslinking agents include (meth)acrylic esters of diols (e.g., butanediol), triols (e.g., glycerol), and tetrols (e.g., pentaerythritol); polymeric multifunctional (meth)acrylates (e.g., poly(ethylene oxide) diacrylate and poly(ethylene oxide) dimethacrylate); polyvinylic compounds (e.g., substituted and unsubstituted divinylbenzene); difunctional urethane acrylates; and mixtures thereof.

When a crosslinking agent is employed to produce a tacky acrylate or vinyl ester microsphere, it is typically used at a level of up to about 0.15 equivalent weight percent. Above about 0.15 equivalent weight percent, the acrylate and vinyl ester microspheres tend to lose their pressure sensitive adhesive qualities and eventually become non-tacky to the touch at room temperature. Both non-tacky and tacky microspheres are useful in this invention. The crosslinking level also affects the ability of the microspheres to swell (i.e., absorb the anti-microbial agent). As the degree of crosslinking increases, the ability of the microsphere to swell decreases. To ensure a high degree of microsphere swelling, it is desirable to use low levels of crosslinker. Crosslinking is also important in achieving the desired release characteristics of the incorporated anti-microbial agent.

The "equivalent weight percent" of a given compound is defined as the number of equivalents of that compound divided by the total number of equivalents of the free radically polymerizable unsaturation in the total microsphere composition. An equivalent is the number of grams divided by the equivalent weight. The equivalent weight is defined as the molecular weight divided by the number of polymerizable groups in the monomer (in the case of those monomers with only one polymerizable group, equivalent weight=molecular weight).

Crosslinking may also be controlled with the use of chain transfer agents. Useful chain transfer agents are those which are normally suited for free radical polymerization of acrylates. The chain transfer agents useful in the practice of the present invention include, but are not limited to, carbon tetrabromide, n-dodecyl mercaptan, isooctylthiolglycolate, and mixtures thereof. If used, the chain transfer agent(s) are present in an amount in the range of from about 0.001 to about 1% by weight of the total polymerizable composition.

Useful oil soluble free radical initiators are those which are normally suitable for free radical polymerization of acrylate or vinyl ester monomers and which are oil soluble and of very low solubility in water, typically less than 1 g/100 g water at 20° C. Examples of such thermal initiators include azo compounds, hydroperoxides, peroxides, and the like. Examples of such photoinitiators include benzophenone, benzoin ethyl ether, 2,2-dimethoxy-2-phenyl acetophenone and the like. The initiator is generally used in an amount in the range of from about 0.01 percent up to about 10 percent by weight of the total polymerizable composition, preferably up to about 5 percent.

The use of a substantially water soluble polymerization initiator, such as those generally used in emulsion polymerization processes, can cause the formation of substantial amounts of latex particles. During suspension polymerization, any significant formation or presence of particles (e.g., latex, inorganic, etc.) can deplete or divert the amount of surfactant available for the polymerization of the monomer. The smaller the particle size, the more significant the reduction in available surfactant.

The elastomeric acrylate or vinyl ester microspheres tend to be bead or pearl shaped, although they may be more spheroidal. Typically, each of these microspheres has a volume average diameter in the range of from about 0.5 to about 300 microns, before the microsphere absorbs or otherwise contains an anti-microbial agent. It can also be desirable for the volume average diameter to be in the range of from about 1 to about 150 microns, or about 1 to about 200 microns. The microspheres may be solid or hollow, or a mixture of both. Hollow microspheres can contain one or more voids; i.e., one or more spaces completely within the walls of the polymerized microsphere. Typically the hollow portion is less than about 100 microns in average diameter. Hollow microspheres may be desirable where the weight of the microspheres is critical for a particular application. It may be desirable for the microspheres to be light weight and hollow, as well as tacky, in order to facilitate their coverage over a desired surface to be protected. If hollow microspheres are desired they may be obtained by either a "two step" process described in U.S. Pat. No. 4,968,562 or a "one step" process as described in U.S. Pat. No. 5,053,436, both of which are incorporated herein by reference in their entirety.

Solid microspheres may be prepared via the suspension polymerization techniques that use ionic or nonionic emulsifiers in an amount sufficient to generate the necessary microsphere size and is generally near the critical micelle concentration.

Each suspension polymerization method (whether producing hollow or solid microspheres) may be modified by withholding the addition of all or some of the free-radically polymerizable polar comonomer until after initiation of the polymerization of the oil phase (meth)acrylic acid ester or vinyl ester. In this instance, however, these components must be added to the polymerizing mixture before 100% conversion of the (meth)acrylic acid ester or vinyl ester monomer. Similarly, a multifunctional free-radically polymerizable crosslinking agent, if used, can be added at any time before 100% conversion to polymer of the monomers of the microsphere composition. Preferably the crosslinking agent is added before initiation occurs.

Anti-Microbial Agents

The anti-microbial material which is associated with the microsphere may be either a liquid or a solid, and is preferably a solid. Solids are first suspended in the monomer mixture or dissolved in a solvent. Solid anti-microbial material is contained in the microsphere following either polymerization or evaporation of the solvent. The solvent is driven off after the solvent/anti-microbial agent solution droplets are trapped within the microsphere. An example of such a solvent evaporation method of making microspheres can be found in a research paper entitled *Interaction between nicardipine hydrochloride and polymeric microspheres for a controlled release system*, by Nilüfer Yüksel, Teoman Tincer and Tamer Baykara, and published in the International Journal of Pharmaceutics 140 (1996), on pages 145–154, which is incorporated in its entirety herein. Liquid agents can also be added to the monomer mixture or added directly, by being allowed to diffuse, into the polymer of the microsphere.

Anti-microbial materials which may be used in this invention include water immiscible or partly miscible compounds. The compounds may be organic or inorganic. Inorganic metal oxides have been found preferable for some applications (e.g., roofing). Anti-microbial materials that are useful with this invention include but are not limited to: metal oxides such as copper oxide, silver oxide, and zinc oxide; other copper salts such as copper chlorides, and copper sulfides; metal powders such as copper, zinc, silver, and tin; powders of metal alloys such as of copper, lead, silver, tin, zinc, and mercury; slightly soluble copper compounds such as cupric stearate, cuprous cyanide, and cuprous mercuric iodide; and the like. Anti-microbial materials that are believed to be useful with this invention include but are not limited to: metal oxides such as lead oxide, titanium dioxide, and platinum oxide; metal sulfides such as lead sulfide and mercury sulfide; water immiscible metal salts such as barium sulfate and barium phosphate; metal powders such as nickel, platinum and manganese; powders of metal alloys such as iron, nickel, antimony, and cadmium; organo-metallic compounds such as tributyl tin oxide, tin acrylates and tin silanes; and the like. Metal oxides such as cuprous oxide have been found to be particularly useful compounds.

Suitable organic anti-microbial agents may include algacides such as 4,5-dicholor-2-n-octyl-4 isothiazolin-3-one (Sea-Nine™ 211) from Rohm and Haas Company of Philadelphia, Pa.; quaternary ammonium salts based anti-microbial materials such as Dow Corning 5700 from Dow Corning Corp of Midland, Mich., and Nopcocide™ N-96 from Henkel Corp. of Ambler, Pa. Other suitable organic anti-microbial agents may include some, if not all, of the agents disclosed in the publication "Industrial Antimicrobial Agents," in Kirk-Othmer, Ed., Encyclopedia of Chemical Technology, John Wiley & Sons, New York, N.Y., Vol. 14, pp. 174–199, which is incorporated herein by reference in its entirety.

The anti-microbial agents may be mixtures of compounds, either inorganic or organic in nature. For example, a partially water miscible anti-microbial agent may be mixed with a water immiscible agent to provide a rapid release followed by a longer, sustained release profile. Such a mixed release profile results because it is its reaction to water that causes each of the anti-microbial agents to move out of the microsphere. The different anti-microbial agents can be present in the same microsphere or each agent can be in its own microsphere and the different microspheres mixed together.

The anti-microbial agent may be in concentrations such as necessary to be effective while not hindering the stability or polymerization of the microspheres. The anti-microbial agent must also be compatible with the components of the microsphere, including the surfactant or stabilization system. It is desirable for the surfactant not to react with or otherwise degrade the anti-microbial agent so as to cause the agent to dissolve into solution. For example, anionic surfactants such as ammonium lauryl sulfate, can cause excessive oxidation of certain metal oxides like cuprous oxide (i.e., $Cu_2O$). The oxidation of cuprous oxide could produce water soluble metal ions resulting in an agglomeration of the microspheres. Therefore, it may be more desirable to use non-ionic stabilizers or surfactants with the type of metal oxide agent that disperses well in heptane (i.e., a metal oxide that has an affinity for non-polar solvents). Microspheres have been made successfully using ammonium lauryl sulfate surfactants with anti-microbial agents other than cuprous oxide (see Example 10). It is believed that surfactants such as poly(vinyl alcohol) can be used with metal oxide anti-microbial agents, like cuprous oxide, because it is believed that such surfactants do not adversely interact with the $Cu_2O$. (e.g., put metal ions into solution).

Other adjuvants can be included in the compositions in amounts needed to effect the desired properties as long as they do not affect the polymerization or the desired end properties or both. Furthermore, such adjuvants can be added to the monomer before being mixed into the water based polymerization solution. It may also be desirable to mix such adjuvants separately into the water solution. Useful adjuvants may include dyes, pigments, fillers, and coupling agents.

The compositions of the invention are typically made by addition of the anti-microbial agent to the monomer mixture or monomer dispersion prior to polymerization. In addition, polymeric dispersing aids are usually not necessary but may be added to help disperse the anti-microbial agent in the monomer mixture.

The present microspheres are useful in the preparation of coated articles, such as tapes, sheets, or more three dimensional structures (e.g., roofing granules). Tapes typically have narrow widths in comparison to length. Sheets typically have substantially equal lengths and widths and may generally be prepared in the same manner as tapes. The tapes can be prepared as transfer tapes, for example, with tacky microspheres coated on one side of a release liner. The liner has release characteristics (e.g., a release coating) on both sides (to allow for rolling of the tape) and functions as the tape backing. The tapes can also be prepared by having the adhesive microspheres permanently adhered to the backing (e.g., a water permeable backing), with a release liner laminated onto the microspheres or the backing provided with release characteristics on its back side. Tapes with the microspheres permanently adhered to the backing can be prepared by first coating the microspheres onto a release liner (e.g., a continuous loop liner) and then transfer the microspheres from the release liner to the backing. Tapes can also be double coated tapes wherein both sides of the backing have a layer of the adhesive microspheres on them. Useful backing materials can include polymeric films, such as those made from cast and oriented polyesters, cast and oriented polypropylene, polyethylene, paper, metal foils, woven and nonwoven fabrics, and foams, such as those made from polyolefins and acrylics. Examples of suitable acrylic foams are those disclosed in U.S. Pat. No. 4,415,615. Suitable polyolefin foams include crosslinked polyethylene and polyethylene/ethylene vinyl acetate (PE/EVA) foams.

The present microspheres, described herein, are also useful as a sprayable composition. The spraying process is safe, fast, less likely to contaminate ground water, results in lower exposure to the environment and other non-target species, and overall has lower labor costs. The ability to spray the present microspheres enables the application of the anti-microbial agent directly to existing structures and devices such as roofs, driveways, decking (wood, concrete, etc.), fencing, siding, patios, surfaces on ships, boats, aircraft, and automobiles, ductwork (A.C. or heating), inside refrigerators, on tents, on sails, etc.

The objects, features, and advantages of the present invention are further illustrated by the examples disclosed below. The particular materials and amounts recited in these examples, as well as other conditions and details, should not be construed to unduly limit this invention. In the below examples, all parts and percentages are by weight, unless otherwise indicated. All molecular weights reported are number average molecular weights.

EXAMPLES

For the below Examples, unless otherwise indicated and as applicable, the iso-octyl acrylate (IOA) used was prepared by one of the following:

Preparation of IOA Polymer Solution—UV Polymerization

In a small glass jar, 0.25 gram of the photoinitiator Irgacure 651, available from Ciba-Geigy of Hawthorne, N.Y., was dissolved in 100.2 grams of iso-octyl acrylate. The solution was degassed by bubbling nitrogen through the solution. Polymerization was effected by exposure to a low intensity UV light while stirring and nitrogen purge. Once the solution had noticeably thickened, the lights were removed and the solution exposed to oxygen. Solids analysis revealed 39% polymer content in the solution.

Preparation of IOA Polymer Solution—Thermal Polymerization

In a reaction flask equipped with an overhead stirrer, nitrogen inlet, and thermocouple, 329.4 gram of the solvent 2-butanone, 100.0 grams of IOA, and 0.24 grams of Luci-dol™ 75 were dissolved. The mixture was heated to 65° C. and degassed. After 17.5 hours at 65° C., the reaction mixture was cooled to room temperature and the 2-butanone stripped off. Iso-octyl acrylate was added to the polymer to constitute a 27% solids solution.

Example 1

25% Polymer Solids Containing 1% $Cu_2O$

A 1 liter (L) reaction flask equipped with an overhead stirrer, nitrogen inlet, and thermocouple was charged with 1.8 grams of the surfactant Airvol™ 540 (i.e., poly(vinyl alcohol) available from Air Products Inc. of Allentown, Pa.) and 452 grams of water. The flask was heated to 65° C. to dissolve the Airvol™ 540. After cooling the reactor to 55° C., 1.5 grams of copper oxide ($Cu_2O$ available from American Chemet Corp. of Deerfield, Ill.) was added to the reactor followed by a preformed mixture containing 148.2 grams of the monomer iso-octyl acrylate (IOA) 1.5 grams of the crosslinker butanedioldiacrylate, and 0.45 grams of the thermoinitiator Vazo 52 (2,2'-azobis(2,4-Dimethylpentane nitrile) available from DuPont of Wilmington, Del.). The agitation speed was set at 400 rpm. The reactor was degassed and heated to a temperature of 65° C. The polymerization reaction is exothermic. Heat from the exothermic reaction caused the reaction t temperature to increase to 79° C. where it was cooled with an ice bath to 69° C. After three hours at 65° C., the purplish/red dispersion was filtered through cheesecloth and collected. Optical microscopy revealed reddish copper oxide particles embedded in solid, spherical microspheres.

Example 2

40% Polymer Solids Containing 5% $Cu_2O$

A 1 L reaction flask equipped with an overhead stirrer, nitrogen inlet, and thermocouple was charged with 4.9 grams of the surfactant Airvol™ 540 and 360.0 grams of water. The flask was heated to 65° C. to dissolve the Airvol™ 540. After cooling the reactor to 55° C., 12.1 grams of copper oxide ($Cu_2O$ available from American Chemet Corp.) was added to the reactor followed by a preformed mixture containing 237.6 grams of iso-octyl acrylate, 2.4 grams of butanedioldiacrylate, and 0.71 grams of of Lucidol™ 75 (75% actives solid of benzoyl peroxide available from Elf Atochem of Philadelphia, Pa.). The agitation speed was set at 600 rpm. The reactor was degassed and heated to a temperature of 65° C. Heat from the exothermic reaction raised the reaction temperature to 79° C. where it was cooled with an ice bath to 69° C. After three hours at 65° C., the purplish/red dispersion was filtered through cheesecloth and collected. Optical microscopy revealed reddish copper oxide particles embedded in solid, spherical microspheres.

Example 3

The following example employed a solution polymer of IOA with the copper oxide. A 1 L reaction flask equipped with an overhead stirrer, nitrogen inlet, and thermocouple was charged with 2.5 grams of the surfactant Airvol™ 540 and 361.8 grams of water. The flask was heated to 65° C. to dissolve the Airvol™ 540. A preformed mixture containing 12.0 grams of copper oxide ($Cu_2O$ available from American Chemet Corp.), 237.56 grams of iso-octyl acrylate (IOA), 2.4 grams of butanedioldiacrylate, 0.71 grams of Lucidol™

75, and 6.3 grams of the above described 39% solids solution of poly(IOA) was added. The agitation speed was set at 500 rpm. The reactor was degassed. After a short time, heat from the exothermic reaction raised the reaction temperature to 80° C. where it was cooled with an ice bath to 69° C. After three hours at 65° C., the purplish/red dispersion was filtered through cheesecloth and collected. Optical microscopy revealed reddish copper oxide particles embedded in solid, spherical microspheres.

Examples 4–9

Examples 4–9 followed the procedure outlined in Example 2.

Example 10

Sea Nine Algacide

A 1 L reaction flask equipped with an overhead stirrer, nitrogen inlet, and thermocouple was charged with 6.0 grams of the surfactant Standapol-A (25% solids solution of ammonium lauryl sulfate in water available from Henkel Inc. of LaGrange, Ill.), 3.0 grams of acrylic acid and 449.9 grams of water. The mixture was then neutralized to a pH>7 by the addition of the neutralizing agent ammonium hydroixde. A preformed mixture containing 145.5 grams of iso-octyl acrylate, 1.6 grams of butanedioldiacrylate, 12.4 grams of the anti-microbial agent (algacide) Sea-Nine™ 211 (4,5-dicholor-2-n-octyl-4 isothiazolin-3-one), a 30% solids solution in xylenes available from Rohm and Haas Company of Philadelphia, Pa., and 0.65 grams of Lucidol™ 75 was added to the water phase. The reaction temperature was raised to 65° C. and the dispersion degassed. After 12 hours at 65° C., the mixture was cooled to room temperature and filtered through cheesecloth. Optical microscopy revealed solid, spherical microspheres.

Example 11

The following example employed a solution polymer of IOA with the copper oxide. A 1 L reaction flask equipped with an overhead stirrer, nitrogen inlet, and thermocouple was charged with 2.4 grams of the surfactant Airvol™ 540 and 360.0 grams of water. The flask was heated to 65° C. to dissolve the Airvol™ 540. A preformed mixture containing 12.0 grams of copper oxide ($Cu_2O$ available from American Chemet Corp.), 220.8 grams of iso-octyl acrylate (IOA), 4.8 grams of 1,4-butanedioldiacrylate, 12.0 grams of n-vinyl pyrrolidinone (NVP), 0.96 grams of Lucidol™ 75, and 8.9 grams of the above described 27% solids solution of poly (IOA) was added. The agitation speed was set at 400 rpm. The reactor was degassed. After a short time, heat from the exothermic reaction raised the reaction temperature to 81° C. where it was cooled with an ice bath to 69° C. After three hours at 65° C., the purplish/red dispersion was filtered through cheesecloth and collected. Optical microscopy revealed reddish copper oxide particles embedded in solid, spherical microspheres.

Example 12

The following example employed a solution polymer of IOA with silver oxide. A 1 L reaction flask equipped with an overhead stirrer, nitrogen inlet, and thermocouple was charged with 2.4 grams of the surfactant Airvol™ 540 and 360.0 grams of water. The flask was heated to 65° C. to dissolve the Airvol™ 540. A preformed mixture containing 12.0 grams of silver oxide, 235.2 grams of iso-octyl acrylate (IOA), 4.8 grams of 1,4-butanedioldiacrylate, 0.96 grams of Lucidol™ 75, and 8.9 grams of the above described 27% solids solution of poly(IOA) was added. The agitation speed was set at 400 rpm. The reactor was degassed. After a short time, heat from the exothermic reaction raised the reaction temperature to 81° C. where it was cooled with an ice bath to 69° C. After three hours at 65° C., the blackish dispersion was filtered through cheesecloth and collected. Optical microscopy revealed black silver oxide particles embedded in solid, spherical microspheres. Particle size analysis revealed an average particle size of 208 microns.

Example 13

The following example employed a solution polymer of IOA with the copper oxide and Sea Nine 211™ algacide. A 1 L reaction flask equipped with an overhead stirrer, nitrogen inlet, and thermocouple was charged with 2.4 grams of the surfactant Airvol™ 540 and 360.0 grams of water. The flask was heated to 65° C. to dissolve the Airvol™ 540. A preformed mixture containing 12.0 grams of copper oxide ($Cu_2O$ available from American Chemet Corp.), 237.6 grams of iso-octyl acrylate (IOA), 2.4 grams of 1,4-butanedioldiacrylate, 40.0 grams of the anti-microbial agent (algacide) Sea-Nine 211™ (30% solids solution in xylenes available from Rohm and Haas Company of Philadelphia, Pa.), 0.36 grams of Lucidol™ 75, and 17.8 grams of the above described 27% solids solution of poly(IOA) was added. The agitation speed was set at 400 rpm. The reactor was degassed. After a short time, heat from the exothermic reaction raised the reaction temperature. After four hours at 65° C., the purplish/red dispersion was filtered through cheesecloth and collected. Optical microscopy revealed reddish copper oxide particles embedded in solid, spherical microspheres. Particle size revealed an average particle size of 163 microns.

Example 14

A 1 L reaction flask equipped with an overhead stirrer, nitrogen inlet, and thermocouple was charged with 2.4 grams of Airvol™ 540 and 360.0 grams of water. The flask was heated to 65° C. to dissolve the Airvol™ 540. A preformed mixture containing 237.7 grams of iso-octyl acrylate, 2.4 grams of the crosslinker 1,4-butanedioldiacrylate (BDA), 0.99 grams of Lucidol™ 75, and 8.9 grams of the above described 27% solids solution of poly(IOA) was added. The agitation speed was set at 400 rpm. The reactor was degassed. After twenty minutes, heat from the exothermic reaction raised the reaction temperature to 81° C. where it was cooled with an ice bath to 69° C. After three hours at 65° C., the white dispersion was filtered through cheesecloth and collected. Optical microscopy revealed solid, spherical microspheres with an average particle size of 140 microns.

To 225.1 grams this dispersion, 30.0 grams of the anti-microbial agent (algacide) Sea-Nine 211™ (30% solids solution in xylenes available from Rohm and Haas Company of Philadelphia, Pa.) was added. The mixture was shaken overnight. Optical microscopy revealed no visible changes to the microspheres.

Each of the microspheres of Examples 1–14 above is made with an elastomeric polymer. Examples 1–4, 7–14 and C1 are non-tacky, and Examples 5 and 6 are tacky. Table 1 below summarizes the copper oxide concentration, monomer composition and average diameter for each of Example 1–9, 11 and C1. Particle size analysis was completed with a Leeds and Northrup Microtrac X100™ particle size analyzer and values reported are the volume average diameter.

TABLE 1

| Example | % Cu$_2$O | Monomer Composition | Ave. Diameter (μm) |
|---------|-----------|---------------------|---------------------|
| 1  | 1  | 99/1 of IOA/BDA      | Approx. 100–160 |
| 2  | 5  | 99/1 of IOA/BDA      | Approx. 100–160 |
| 3  | 5  | 99/1 of IOA/BDA      | 141 |
| 4  | 10 | 99/1 of IOA/BDA      | 174 |
| 5  | 5  | 100 IOA              | 109 |
| 6  | 5  | 100 IOA              | 131.5 |
| 7  | 25 | 99/1 of IOA/BDA      | 273 |
| 8  | 5  | 99/1 of IOA/BDA      | 9.2 |
| 9  | 5  | 99/1 IOA/BDA         | 62.7 |
| 11 | 5  | 93/2/5 IOA/BDA/NVP   | 210 |
| C1 | 5  | 99/1 of IOA/BDA      | 85 |

Comparative Example C1

Post Add Copper Oxide

A 1 L reaction flask equipped with an overhead stirrer, nitrogen inlet, and thermocouple was charged with 2.4 grams of Airvol™ 540 and 360.0 grams of water. The flask was heated to 65° C. to dissolve the Airvol™ 540. A preformed mixture containing 237.3 grams of iso-octyl acrylate, 2.4 grams of the crosslinker 1,4-butanedioldiacrylate (BDA), 0.94 grams of Lucidol™ 75, and 8.8 grams of the above described 27% solids solution of poly(IOA) was added. The agitation speed was set at 450 rpm. The reactor was degassed. After twenty minutes, heat from the exothermic reaction raised the reaction temperature to 82° C. where it was cooled with an ice bath to 67° C. After three hours at 65° C., the white dispersion was filtered through cheesecloth and collected. Optical microscopy revealed solid, spherical microspheres.

To this dispersion, 12.0 grams of copper oxide (Cu$_2$O available from American Chemet Corp.) was added. The mixture was shaken overnight to disperse the copper oxide particles. Optical microscopy revealed copper oxide particles evenly dispersed throughout the sample. However, no affinity of the copper for the microspheres was seen. That is, the Cu$_2$O particles did not appear to be embedded in or otherwise attached to the microspheres.

Comparative Example 2

Solution Polymer with Cu$_2$O

In a reaction flask equipped with an overhead stirrer, nitrogen inlet, and thermocouple, 262.4 grams of 2-butanone, 86.64 grams of IOA, 0.84 grams of BDA, 4.35 grams of Cu$_2$O, and 0.26 grams of Lucidol™ 75. With stirring, the mixture was heated to 65° C. and degassed. After 12 hours at 65° C., the reaction mixture was cooled to room temperature.

Comparative Example 3

Copper Oxide with Stepanol

A 1 L reaction flask equipped with an overhead stirrer, nitrogen inlet, and thermocouple was charged with 6.0 grams of the surfactant Stepanol AMV (29% solids solution of ammonium lauryl sulfate available from Stepan Co. of Northfield, Ill.) and 450.8 grams of water. A mixture of poly(IOA) in IOA monomer and copper oxide was prepared by the addition of 38.67 g of the above described 39% poly(IOA) solution in IOA to 20.37 grams of copper oxide. 14.81 grams of this copper oxide/poly(IOA) solution was added to a preformed mixture containing 147.1 grams of iso-octyl acrylate, 3.0 grams of butanedioldiacrylate. The copper oxide/monomer phase was added to the water phase and the mixture heated to 50° C. and degassed while the agitation speed was set at 400 rpm. Then 0.44 grams of the Vazo 52 initiator was added to the reaction vessel and the mixture degased again and heated to 65° C. After only 5 minutes, heat from the exothermic reaction raised the reaction temperature to 82° C. where it was cooled with an ice water bath. During the exothermic rise in temperature, the copper oxide visibly precipitated and the resulting polymer coagulated. This example illustrates the importance of choosing the proper stabilizing system (e.g., surfactant) during the polymerization.

Comparative Example 4

Copper Oxide with Surfactant

A 1 L reaction flask equipped with an overhead stirrer, nitrogen inlet, and thermocouple was charged with 360.0 grams of water. A preformed mixture containing 237.6 grams of iso-octyl acrylate, 2.5 grams of butanedioldiacrylate, 12.0 grams of copper oxide, and 0.96 grams of Lucidol™ 75 was added to the water. The agitator speed was set at 400 rpm and the reaction heated to 65° C. The reaction immediately coagulated upon reaching 65° C. This example illustrates that the copper oxide fails to stabilize polymer particles.

Inorganic Agent Release Test Method

The following test method was used to evaluate the controlled release performance of microspheres containing inorganic anti-microbial agent such as copper oxide. This test is applicable whether the inorganic agent was incorporated in particle form or by being dissolved in a solvent. The basic test concept is to leach the anti-microbial agent from the microspheres into water for specific periods of time and then use inductively coupled plasma spectroscopy (ICP) to measure the level of the inorganic material released. Preferably, the water used is de-ionized or at least has a low ion content.

The general procedure followed for this test is to coat out onto a suitable substrate, such as polystyrene or glass, and thoroughly dry a nominal amount of the microspheres to be tested. The dry weight of the coating is measured. A known amount of the anti-microbial agent is incorporated into the microspheres. The dried microsphere samples are then placed in a known weight of water with moderate stirring for an arbitrary period of time, for example, 24 hours and 168 hours. At the end of the prescribed period of time the microsphere sample is removed from the resulting leachate (i.e., water solution). The leachate is then filtered to remove any particulate matter such as loose microspheres. The collected weight of leachate is measured. ICP is then used to determine the total amount of copper or copper concentration in the leachate. Additionally, if the microspheres are left for a significant period of time in the water used for the polymerization, a filtered sample of the polymerization water may also be measured via ICP for copper content to determine the amount of copper, if any, released from the microspheres prior to the above described testing. The rate at which copper is released from the microsphere sample is then calculated by dividing the amount of anti-microbial agent released by the time the particles were in the water. Table 2 reports the release data of copper into de-ionized water at 24 hours and 168 hours in ppm or (μg Cu released/g leachate) of copper in the leachate per gram of coating.

TABLE 2

Release Results

| Example | Time = 24 hours (ppm Cu/g of coating) | Time = 168 hours (ppm Cu/g of coating) |
| --- | --- | --- |
| 1 | 0.63 | 1.5 |
| 2 | 2.1 | 2.9 |
| 3 | 4.5 | 7.9 |
| 4 | 4.5 | 11.0 |
| 5 | 4.1 | 5.6 |
| 6 | 4.8 | 5.9 |
| 7 | 4.2 | 16.0 |
| 8 | 6.0 | 7.8 |
| 9 | 1.6 | 3.1 |
| C1 | 1.4 | 2.6 |
| C2 | 0.23 | 0.29 |
| De-ionized Water | <0.04 ppm Cu | <0.04 ppm Cu |

Organic Agent Release Test Method

The following test method was used to determine the release performance of microspheres containing the organic anti-microbial agent of Example 10 (i.e., Sea-Nine). The basic test concept is to coat the microspheres on to a substrate such as roofing granules and place a known amount of the coated material into a closed container with an inoculum of algae. After a nominal growth period in a controlled environment the relative amounts of growth in the control and test samples are determined by measuring the light absorbance of the growth medium using a UV-Visible range spectrophotometer. The amount of light absorbed is proportional to the amount of algae in the sample. Samples are run in triplicate using the unicellular green alga, *Neochloris*.

The microspheres were coated onto roofing granules (product designation LR9300 from 3M Company, St. Paul, Minn.). Two controls were used for comparison. Control 1 was the roofing granules without any microsphere coating. Control 2 was the roofing granules with a coating of microspheres that do not contain any anti-microbial agent. Relative to the controls, a lower absorbance value indicates that a lower amount of alga growth occurred in the test sample, which is indicative of the effectiveness of the sample. Note that absorbance is a relative scale from 0 to 1 where 0 is the absorbance of only de-ionized water.

The absorbance results for the microspheres described in Example 10 and those of Control 1 and 2 are as follows: The Control 1 microspheres had an absorbance of 0.58; the Control 2 had an absorbance of 0.30; and the Example 10 microspheres had an absorbance of 0.02. These results show that the microspheres in example 10 are releasing a sufficient amount of the Sea-Nine anti-microbial agent to effectively inhibit the growth of this algae.

Attachment of Microspheres to a Substrate

Attachment Example 1

Tacky Adhesive Microspheres of Examples 5 and 6

Microspheres were formulated with a crosslink density such that the surface of the spheres remains tacky after reaction, in accordance with Examples 5 and 6 above. These microspheres can then be coated onto a substrate where they are firmly attached due to the adhesive nature of the microsphere surface. An example of this was carried out by coating tacky microspheres onto a standard aphalt roofing shingle and onto standard Roofing Granules manufactured by 3M Company. In the case of the asphalt shingle, the microspheres were coated onto the granule laden surface of the shingle by use of a foam paint brush. The coating could also be applied by a spray system, or any other method suitable for delivering a uniform coverage of the water based microspheres onto the shingles. The water was then dried off leaving the microspheres firmly attached and uniformly distributed across the shingle surface with only a slight but uniform yellowing of the original color and appearance of the shingle. However the surface the shingle tended to by slightly tacky to the touch. It is believed that this effect can be altered by the level of microsphere coverage and the degree of crosslinking in the microspheres.

The same adhesive microsphere formulation was also coated onto loose ceramic coated roofing granules such as those manufactured be 3M Company. The loose granules were coated by pipetting a volume of the water suspension of microspheres onto the granules and tumbling the granules so as to coat all sides. The coated granules were allowed to dry. The microspheres were found to be firmly attached to the granules even when submersed in de-ionized water. The tacky nature of the microspheres tended to cause the individual granules to stick together. It is believed that this effect can also be altered by the level of microsphere coverage and the degree of crosslinking in the microspheres.

Attachment Example 2

Use of Primers to Adhere Non-Tacky Microspheres

By increasing their crosslink density, the microspheres were rendered non-tacky upon drying. Repeating the coating procedures described in Attachment Example 1, these microspheres did not firmly attach to either the shingle or the loose granules, especially in the presence of water. In order to improve the adhesion of these non-tacky microspheres to various substrates a bonding layer (e.g., a primer coat) was introduced. The primer was first coated onto the shingle or granule substrate similar to the method described in Attachment Example 1 for the application of the microspheres and allowed to dry. Then as a second application step the non-tacky microspheres were coated out of water onto the primed substrate, again using the methods described in Attachment Example 1.

Suitable primers include core-shell latexes as described in U.S. Pat. No. 5,461,125 or aminated polybutadienes (APB) as described in U.S. Pat. No. 3,661,874, both of which are incorporated herein by reference. The APB gave improved adhesion results over unprimed non-tacky microsphere coatings on loose granules. The APB primer did not appear to interfere with the asphalt shingle and resulted in only a slight yellow discoloration from the original shingle color. There was not any noticeable discoloration of the loose granules due to the primer. It is believed that any of a variety of primers that are stable (i.e., compatible) with both the substrate of choice and the microsphere would be suitable.

Attachment Example 3

Microspheres in a Clear Coat

The microsphere formulation described in Example 8 above was dispersed into a film forming water-based polyurethane. This combination was then coated onto loose 3M roofing granules in the method described in Attachment Example 1 and allowed to dry. This was found to firmly adhere the non-tacky microspheres to the granule surface with minimal discoloration of the granules. Any of a wide variety of polymer coatings are believed to be suitable for use in accordance with the method of this attachment example. The basic premise is that a polymer coating initially separate from the microspheres is used to adhere the microspheres to a given substrate. Preferably, the coating is clear so as not to affect the original color or appearance of the substrate.

From the above disclosure of the general principles of the present invention and the preceding detailed description, those skilled in this art will readily comprehend the various modifications and uses to which the present invention is susceptible. For example, the ability to spray, brush on or otherwise apply the polymer particles of the present delivery system enables the application of the anti-microbial agent directly to existing structures and devices. Uses for the present anti-microbial delivery system include, but are not limited to, being applied to roofs (e.g., on asphalt, wood and plastic shingles; ceramic and metal tile; slate; bituminous roofing membranes; metal sheeting; roll roofing; etc) and other building structures (e.g., interior wall and ceilings), decking (wood, concrete, etc.), fencing, siding, patios, surfaces on ships, boats, aircraft, and automobiles, outdoor furniture, ductwork (air conditioning or heating), inside of refrigeration units, cooling towers, on tents, on sails, animal cages, etc. Basically, it appears that the present anti-microbial delivery system can be used to protect any structure or device on which the present polymer particles can be applied.

In addition, by making the polymeric particles of the present delivery system hollow or otherwise light weight, coverage over a desired surface to be protected can be facilitated. For example, their relative light weight may enable such microspheres (hollow or maybe even solid) to be carried by the air circulating through an air conditioning or heating duct to a remote or otherwise inaccessible surface.

It is also contemplated that the present polymeric particles can be mixed in with tile grout, concrete, etc. and allowed to set in place. The porous nature of these materials will likely allow for the release of the anti-microbial agent. It is further contemplated as desirable to spray or otherwise apply adhesive polymer particles according to the present invention onto a tent or sail or the like before folding it for storage. storing tent, sails, etc. Another potential use of the present delivery system is to sterilize or maintain the sterility of surfaces such as in hospitals (e.g., in operating rooms).

Yet another use of the present delivery system involves forming a tape with about one inch (2.54 cm) wide strips of backing material (e.g., a transparent backing) coated with the present microspheres. The tape can be secured under the lower edge of a row of roofing shingles on a previously shingled roof or attached along the bottom edge of each shingle before the shingle is secured to a roof Therefore, the scope of the present invention should be limited only by the following claims and equivalents thereof.

What is claimed is:

1. An anti-microbial delivery system for delivering an anti-microbial agent to a surface in a time release manner, said delivery system comprising:
a polymeric elastomeric and swellable microsphere containing an anti-microbial agent incorporated therein so as to be releasable from the boundary of said polymeric elastomeric and swellable microsphere in an effective amount for anti-microbial efficacy over time when said polymeric elastomeric and swellable microsphere is in the presence of water and such that the agent is not released when the polymeric elastomeric and swellable microsphere is not in the presence of water, wherein the polymeric elastomeric and swellable microsphere has a diameter of about 0.5 to about 300 micrometers wherein said anti-microbial agent comprises a material selected from the group consisting of metal oxides, metal powders, powders of metal alloys, copper compounds, metal sulfides, metal salts, organo-metallic compounds and combinations thereof.

2. The delivery system of claim 1, wherein said anti-microbial agent is copper oxide.

3. The delivery system of claim 1, wherein said anti-microbial agent is a plurality of inorganic particles incorporated into said polymeric elastomeric and swellable microsphere.

4. The delivery system of claim 1, wherein said anti-microbial agent provides up to about 40% by weight of the total weight of said microsphere and said anti-microbial agent.

5. The delivery system of claim 1, wherein said polymer elastomeric and swellable microsphere is adhesively tacky.

6. The delivery system of claim 1, wherein said polymeric elastomeric and swellable microsphere contains at least one hollow cavity therein.

7. An anti-microbial delivery system for delivering an anti-microbial agent to a surface in a time release manner, said delivery system comprising:
a polymeric elastomeric and swellable microsphere containing an anti-microbial agent incorporated therein so as to be releasable from the boundary of said polymeric elastomeric and swellable microsphere in an effective amount for anti-microbial efficacy over time when said polymeric elastomeric and swellable microsphere is in the presence of water and such that the agent is not released when the polymeric elastomeric and swellable microsphere is not in the presence of water, wherein the polymeric elastomeric and swellable microsphere has a diameter of about 0.5 to about 300 micrometers and contains an anti-microbial agent comprising copper oxide.

8. The delivery system of claim 7, wherein said anti-microbial agent further comprises an organic material.

9. The delivery system of claim 7, wherein said anti-microbial agent is a plurality of copper oxide particles incorporated into said polymeric elastomeric and swellable microsphere.

10. The delivery system of claim 7, wherein said anti-microbial agent provides up to about 40% by weight of the total weight of said microsphere and said anti-microbial agent.

11. The delivery system of claim 7, wherein said polymer elastomeric and swellable microsphere is adhesively tacky.

12. The delivery system of claim 7, wherein said polymeric elastomeric and swellable microsphere contains at least one hollow cavity therein.

13. An anti-microbial delivery system for delivering an anti-microbial agent to a surface in a time release manner, said delivery system comprising:

a polymeric elastomeric and swellable microsphere containing an anti-microbial agent incorporated therein so as to be releasable from the boundary of said polymeric elastomeric and swellable microsphere in an effective amount for anti-microbial efficacy over time when said polymeric elastomeric and swellable microsphere is in the presence of water and such that the agent is not released when the polymeric elastomeric and swellable microsphere is not in the presence of water, wherein the polymeric elastomeric and swellable microsphere has a diameter of about 0.5 to about 300 micrometers and contains an anti-microbial agent wherein said anti-microbial agent comprises a plurality of inorganic particles incorporated into said polymeric elastomeric and swellable microsphere.

14. The delivery system of claim 13, wherein said anti-microbial agent further comprises an organic material.

15. The delivery system of claim 13, wherein said anti-microbial agent comprises a material selected from the group consisting of metal oxides, metal powders, powders of metal alloys, copper compounds, metal sulfides, metal salts, organo-metallic compounds and combinations thereof.

16. The delivery system of claim 13, wherein said anti-microbial agent is copper oxide.

17. The delivery system of claim 13, wherein said anti-microbial agent provides up to about 40% by weight of the total weight of said microsphere and said anti-microbial agent.

18. The delivery system of claim 13, wherein said polymer elastomeric and swellable microsphere is adhesively tacky.

19. The delivery system of claim 13, wherein said polymeric elastomeric and swellable microsphere contains at least one hollow cavity therein.

* * * * *